US012758764B2

(12) United States Patent
Edwards et al.

(10) Patent No.: US 12,758,764 B2
(45) Date of Patent: Oct. 13, 2026

(54) PERCUTANEOUS CIRCULATORY SUPPORT SYSTEMS AND DEVICES INCLUDING AORTIC VALVE INSUFFICIENCY DETECTION

(71) Applicant: Boston Scientific Scimed, Inc., Maple Grove, MN (US)

(72) Inventors: Nathan Edwards, Minneapolis, MN (US); Corydon Carlson, Stillwater, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 139 days.

(21) Appl. No.: 18/618,425

(22) Filed: Mar. 27, 2024

(65) Prior Publication Data

US 2024/0325720 A1 Oct. 3, 2024

Related U.S. Application Data

(60) Provisional application No. 63/455,934, filed on Mar. 30, 2023.

(51) Int. Cl.
*A61M 60/546* (2021.01)
*A61M 60/178* (2021.01)
(Continued)

(52) U.S. Cl.
CPC ........ *A61M 60/546* (2021.01); *A61M 60/178* (2021.01); *A61M 60/216* (2021.01);
(Continued)

(58) Field of Classification Search
CPC .............. A61M 60/531; A61M 60/216; A61M 60/538; A61M 60/122; A61M 60/178;
(Continued)

(56) References Cited

U.S. PATENT DOCUMENTS 4,957,504 A 9/1990 Chardack
5,021,048 A 6/1991 Buckholtz
(Continued)

FOREIGN PATENT DOCUMENTS

CN 113945867 A * 1/2022 ......... G01R 31/1209
EP 1046403 A1 10/2000
(Continued)

OTHER PUBLICATIONS

US 9,067,007 B2, 06/2015, Tanner et al. (withdrawn)
(Continued)

*Primary Examiner* — Igor N Borissov
(74) *Attorney, Agent, or Firm* — Seager, Tufte & Wickhem LLP

(57) ABSTRACT

A percutaneous circulatory support system includes an impeller and a motor operably coupled to the impeller. A controller is operably coupled to the motor, and the controller is configured to: drive the motor, the motor thereby rotating the impeller to cause blood to flow; determine that an operating parameter of the system deviates from a symmetric waveform; and in response to determining that the operating parameter deviates from the symmetric waveform, provide an alert of aortic valve insufficiency.

20 Claims, 7 Drawing Sheets

(51) Int. Cl.

| | |
|---|---|
| ***A61M 60/216*** | (2021.01) |
| ***A61M 60/411*** | (2021.01) |
| ***A61M 60/531*** | (2021.01) |
| ***A61M 60/816*** | (2021.01) |

(52) U.S. Cl.

CPC ........ *A61M 60/411* (2021.01); *A61M 60/531* (2021.01); *A61M 60/816* (2021.01); *A61M 2205/10* (2013.01); *A61M 2205/18* (2013.01); *A61M 2205/3303* (2013.01); *A61M 2205/3327* (2013.01); *A61M 2205/3331* (2013.01); *A61M 2205/3365* (2013.01); *A61M 2205/50* (2013.01); *A61M 2210/125* (2013.01)

(58) Field of Classification Search

CPC ......................... A61M 60/546; A61M 60/816; A61M 60/411; A61M 2205/3331; A61M 2205/50; A61M 2205/3327; A61M 2210/125; A61M 2205/3303; A61M 2205/18; A61M 2205/3365; A61M 2205/10

USPC ........................................................... 600/16

See application file for complete search history.

(56) References Cited

U.S. PATENT DOCUMENTS

| | | | |
|---|---|---|---|
| 5,145,333 | A | 9/1992 | Smith |
| 5,211,546 | A | 5/1993 | Isaacson et al. |
| 5,376,114 | A | 12/1994 | Jarvik |
| 5,399,145 | A | 3/1995 | Ito et al. |
| 5,507,629 | A | 4/1996 | Jarvik |
| 5,527,159 | A | 6/1996 | Bozeman, Jr. et al. |
| 5,531,789 | A | 7/1996 | Yamazaki et al. |
| 5,611,679 | A | 3/1997 | Ghosh et al. |
| 5,692,882 | A | 12/1997 | Bozeman, Jr. et al. |
| 5,928,131 | A | 7/1999 | Prem |
| 5,947,703 | A | 9/1999 | Nojiri et al. |
| 5,947,892 | A | 9/1999 | Benkowski et al. |
| 5,964,694 | A | 10/1999 | Siess et al. |
| 6,007,478 | A | 12/1999 | Siess et al. |
| 6,056,520 | A | 5/2000 | Nguyen et al. |
| 6,135,729 | A | 10/2000 | Aber |
| 6,139,487 | A | 10/2000 | Siess |
| 6,176,822 | B1 | 1/2001 | Nix et al. |
| 6,176,848 | B1 | 1/2001 | Rau et al. |
| 6,201,329 | B1 | 3/2001 | Chen |
| 6,227,820 | B1 | 5/2001 | Jarvik |
| 6,264,635 | B1 | 7/2001 | Wampler et al. |
| 6,301,329 | B1 | 10/2001 | Surridge |
| 6,447,266 | B2 | 9/2002 | Antaki et al. |
| 7,010,954 | B2 | 3/2006 | Siess et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,007,254 | B2 | 8/2011 | Larose et al. |
| 8,043,074 | B2 | 10/2011 | Tada |
| 8,376,707 | B2 | 2/2013 | McBride et al. |
| 8,512,012 | B2 | 8/2013 | Akdis et al. |
| 8,591,393 | B2 | 11/2013 | Walters et al. |
| 8,597,170 | B2 | 12/2013 | Walters et al. |
| 8,684,904 | B2 | 4/2014 | Campbell et al. |
| 8,721,517 | B2 | 5/2014 | Zeng et al. |
| 8,770,945 | B2 | 7/2014 | Ozaki et al. |
| 8,827,661 | B2 | 9/2014 | Mori |
| 8,992,163 | B2 | 3/2015 | McBride et al. |
| 9,067,005 | B2 | 6/2015 | Ozaki et al. |
| 9,072,825 | B2 | 7/2015 | Pfeffer et al. |
| 9,091,271 | B2 | 7/2015 | Bourque |
| 9,138,518 | B2 | 9/2015 | Yuen et al. |
| 9,162,017 | B2 | 10/2015 | Evans et al. |
| 9,199,020 | B2 | 12/2015 | Siess |
| 9,308,302 | B2 | 4/2016 | Zeng |
| 9,308,304 | B2 | 4/2016 | Peters et al. |
| 9,314,557 | B2 | 4/2016 | Ricci et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,364,594 | B2 | 6/2016 | Nüsser et al. |
| 9,381,288 | B2 | 7/2016 | Schenck et al. |
| 9,398,743 | B1 | 7/2016 | Fox et al. |
| 9,421,311 | B2 | 8/2016 | Tanner et al. |
| 9,446,179 | B2 | 9/2016 | Keenan et al. |
| 9,474,840 | B2 | 10/2016 | Siess |
| 9,616,157 | B2 | 4/2017 | Akdis |
| 9,669,142 | B2 | 6/2017 | Spanier et al. |
| 9,675,740 | B2 | 6/2017 | Zeng et al. |
| 9,717,833 | B2 | 8/2017 | McBride et al. |
| 9,737,652 | B2 | 8/2017 | Larose et al. |
| 9,770,543 | B2 | 9/2017 | Tanner et al. |
| 9,872,947 | B2 | 1/2018 | Keenan et al. |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Yuen et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,117,980 | B2 | 11/2018 | Keenan et al. |
| 10,149,932 | B2 | 12/2018 | McBride et al. |
| 10,215,187 | B2 | 2/2019 | McBride et al. |
| 10,232,099 | B2 | 3/2019 | Peters et al. |
| 10,251,985 | B2 | 4/2019 | Larose et al. |
| 10,251,986 | B2 | 4/2019 | Larose et al. |
| 10,478,539 | B2 | 11/2019 | Pfeffer et al. |
| 10,478,540 | B2 | 11/2019 | Scheckel et al. |
| 10,525,178 | B2 | 1/2020 | Zeng |
| 10,576,192 | B2 | 3/2020 | Muller et al. |
| 10,576,193 | B2 | 3/2020 | Tanner et al. |
| 10,704,553 | B2 | 7/2020 | Janeczek et al. |
| 10,709,829 | B2 | 7/2020 | Muller |
| 10,709,830 | B2 | 7/2020 | Tanner et al. |
| 10,765,789 | B2 | 9/2020 | Zeng et al. |
| 10,765,791 | B2 | 9/2020 | Moyer et al. |
| 10,780,208 | B2 | 9/2020 | Siess et al. |
| 10,786,610 | B2 | 9/2020 | Zeng |
| 10,799,624 | B2 | 10/2020 | Pfeffer et al. |
| 10,835,654 | B2 | 11/2020 | Harjes et al. |
| 10,842,921 | B2 | 11/2020 | Siess et al. |
| 10,864,308 | B2 | 12/2020 | Muller et al. |
| 10,864,309 | B2 | 12/2020 | McBride et al. |
| 10,874,783 | B2 | 12/2020 | Pfeffer et al. |
| 10,894,115 | B2 | 1/2021 | Pfeffer et al. |
| 10,918,774 | B2 | 2/2021 | Stanfield et al. |
| 10,960,116 | B2 | 3/2021 | Yuen et al. |
| 10,960,118 | B2 | 3/2021 | Sunagawa |
| 10,973,967 | B2 | 4/2021 | Nyikos et al. |
| 10,980,927 | B2 | 4/2021 | Pfeffer et al. |
| 11,027,114 | B2 | 6/2021 | D'Ambrosio et al. |
| 11,033,727 | B2 | 6/2021 | Tuval et al. |
| 11,058,865 | B2 | 7/2021 | Fitzgerald et al. |
| 11,097,092 | B2 | 8/2021 | Siess et al. |
| 11,107,626 | B2 | 8/2021 | Siess et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,185,677 | B2 | 11/2021 | Salahieh et al. |
| 11,219,755 | B2 | 1/2022 | Siess et al. |
| 11,229,786 | B2 | 1/2022 | Zeng et al. |
| 11,235,138 | B2 | 2/2022 | Gross-Hardt et al. |
| 11,253,693 | B2 | 2/2022 | Pfeffer et al. |
| 11,260,213 | B2 | 3/2022 | Zeng et al. |
| 11,273,301 | B2 | 3/2022 | Pfeffer et al. |
| 11,298,524 | B2 | 4/2022 | El Katerji et al. |
| 11,311,712 | B2 | 4/2022 | Zeng et al. |
| 11,338,124 | B2 | 5/2022 | Pfeffer et al. |
| 11,357,967 | B2 | 6/2022 | Zeng et al. |
| 11,400,276 | B2 | 8/2022 | Chopra et al. |
| 11,471,664 | B2 | 10/2022 | Xu et al. |
| 11,497,896 | B2 | 11/2022 | Tanner et al. |
| 11,517,736 | B2 | 12/2022 | Earles et al. |

(56) References Cited

U.S. PATENT DOCUMENTS

| | | | | |
|---|---|---|---|---|
| 11,529,062 | B2 | 12/2022 | Moyer et al. | |
| 11,569,015 | B2 | 1/2023 | Mourran et al. | |
| 11,583,659 | B2 | 2/2023 | Pfeffer et al. | |
| 11,628,294 | B2 | 4/2023 | Chopra et al. | |
| 11,648,388 | B2 | 5/2023 | Siess et al. | |
| 11,672,968 | B2 | 6/2023 | Antaki | |
| 11,708,833 | B2 | 7/2023 | McBride et al. | |
| 11,754,075 | B2 | 9/2023 | Schuelke et al. | |
| 11,786,700 | B2 | 10/2023 | Pfeffer et al. | |
| 11,813,443 | B2 | 11/2023 | Hanson et al. | |
| 12,029,891 | B2 * | 7/2024 | Siess | A61M 60/13 |
| 2003/0233021 | A1 | 12/2003 | Nose et al. | |
| 2004/0191116 | A1 | 9/2004 | Jarvik et al. | |
| 2005/0267322 | A1 | 12/2005 | LaRose | |
| 2006/0222533 | A1 | 10/2006 | Reeves et al. | |
| 2008/0114339 | A1 | 5/2008 | McBride et al. | |
| 2009/0060743 | A1 | 3/2009 | McBride et al. | |
| 2009/0093764 | A1 | 4/2009 | Pfeffer et al. | |
| 2009/0171137 | A1 | 7/2009 | Farnan et al. | |
| 2011/0224655 | A1 | 9/2011 | Asirvatham et al. | |
| 2011/0237863 | A1 | 9/2011 | Ricci et al. | |
| 2011/0238172 | A1 | 9/2011 | Akdis | |
| 2013/0338559 | A1 | 12/2013 | Franano et al. | |
| 2014/0005467 | A1 | 1/2014 | Farnan et al. | |
| 2014/0010686 | A1 | 1/2014 | Tanner et al. | |
| 2014/0336446 | A1 | 11/2014 | Rodefield | |
| 2016/0271308 | A1 | 9/2016 | Larose et al. | |
| 2017/0043074 | A1 | 2/2017 | Siess | |
| 2017/0055908 | A1 | 3/2017 | Radman et al. | |
| 2017/0128646 | A1 | 5/2017 | Karch | |
| 2017/0296725 | A1 | 10/2017 | Peters et al. | |
| 2018/0303990 | A1 | 10/2018 | Siess et al. | |
| 2018/0311423 | A1 | 11/2018 | Zeng et al. | |
| 2018/0353667 | A1 | 12/2018 | Moyer et al. | |
| 2019/0053714 | A1 | 2/2019 | Guelen et al. | |
| 2019/0160213 | A1 * | 5/2019 | Wampler | A61B 5/318 |
| 2019/0275224 | A1 | 9/2019 | Hanson et al. | |
| 2020/0030510 | A1 | 1/2020 | Higgins | |
| 2020/0306434 | A1 | 10/2020 | VanCamp et al. | |
| 2020/0360582 | A1 | 11/2020 | Siess et al. | |
| 2021/0015982 | A1 | 1/2021 | Kerkhoffs et al. | |
| 2021/0023282 | A1 | 1/2021 | Siess et al. | |
| 2021/0038785 | A1 | 2/2021 | Siess et al. | |
| 2021/0069392 | A1 | 3/2021 | Muller et al. | |
| 2021/0069393 | A1 | 3/2021 | Schauer et al. | |
| 2021/0106810 | A1 | 4/2021 | Pfeffer et al. | |
| 2021/0187270 | A1 | 6/2021 | Schenck et al. | |
| 2021/0275794 | A1 | 9/2021 | Sunagawa | |
| 2021/0290164 | A1 | 9/2021 | Linder et al. | |
| 2021/0322757 | A1 | 10/2021 | D'Ambrosio | |
| 2022/0134082 | A1 | 5/2022 | Pfeffer et al. | |
| 2022/0167862 | A1 | 6/2022 | Edelman et al. | |
| 2022/0384070 | A1 | 12/2022 | Mourran | |
| 2023/0040593 | A1 | 2/2023 | Liu et al. | |
| 2023/0131738 | A1 * | 4/2023 | Alwatban | A61M 60/178 600/17 |
| 2023/0149699 | A1 | 5/2023 | Beekman et al. | |

FOREIGN PATENT DOCUMENTS

| | | | |
|---|---|---|---|
| EP | 0847767 | B1 | 2/2005 |
| EP | 2301598 | B1 | 7/2017 |
| EP | 2145638 | B1 | 9/2021 |
| EP | 3352808 | B1 | 9/2023 |
| JP | 2021531136 | A | 11/2021 |
| WO | 9500185 | A1 | 1/1995 |
| WO | 0117581 | A2 | 3/2001 |
| WO | 2018197306 | A1 | 11/2018 |
| WO | 2019135767 | A1 | 7/2019 |
| WO | 2021113389 | A1 | 6/2021 |

OTHER PUBLICATIONS

Khalid A. Alonazi, Nigel H. Lovell, Fellow, IEEE, and Socrates Dokos, "Simulation of motor current waveforms in monitoring aortic valve state during ventricular assist device support"; Member, IEEE; 978-1-4577-0220-4/16/$31 © 2016 IEEE pp. 1451-1454.*

Jonathan D. Rich and Daniel Burkhoff; "HVAD Flow Waveform Morphologies: Theoretical Foundation and Implications for Clinical Practice"; ASAIO Journal 2017; pp. 526-535.*

International Search Report and Written Opinion for International Application No. PCT/US2024/021674, dated Jun. 24, 2024. (11 pages).

Acharya et al., "Aortic Valve Disorders and Left Ventricular Assist Devices," Frontiers in Cardiovascular Medicine, 13 pages, Published Feb. 23, 2023.

Hayward et al., "Pump Speed Waveform Analysis to Detect Aortic Valve Opening in Patients on Ventricular Assist Device Support," Artificial Organs, vol. 39, No. 8, pp. 704-709. Aug. 2015. (Abstract Only).

Imamura et al., "Estimation of the Severity of Aortic Insufficiency by HVAD Flow Waveform," The Annals of Thoracic Surgery, vol. 109, No. 3, pp. 945-949. Mar. 2020.

* cited by examiner

PERCUTANEOUS CIRCULATORY SUPPORT SYSTEMS AND DEVICES INCLUDING AORTIC VALVE INSUFFICIENCY DETECTION

CROSS REFERENCE TO RELATED APPLICATIONS

This application claims the benefit of U.S. Provisional Patent Application Ser. No. 63/455,934, filed Mar. 30, 2023, which is incorporated herein by reference.

TECHNICAL FIELD

The present disclosure relates to percutaneous circulatory support systems and devices. More specifically, the disclosure relates to percutaneous circulatory support systems and devices capable of detecting aortic valve insufficiency, also referred to as aortic regurgitation.

BACKGROUND

Percutaneous circulatory support devices, or blood pumps, can provide transient support for up to several weeks in patients with compromised heart function or cardiac output. Some of these devices, specifically left ventricular support devices, facilitate blood flow from the left ventricle, across the aortic valve, and into the aorta. However, use of left ventricular support devices can cause aortic valve insufficiency, in which the aortic valve fails to properly seal and isolate the left ventricle and the aorta during diastole. For fully implanted/long term left ventricular support devices, aortic valve insufficiency can develop because the heart loses pulsatility during systole due to the ventricular pressure not reaching sufficient levels to open the leaflets of the aortic valve. The leaflets can fuse together, and the valve can degrade and provide diminished sealing functionality. In these situations, left ventricular support devices indirectly impact the valvular function by altering ventricular contractility. Aortic insufficiency can also occur acutely during use of short term left ventricular support devices that are positioned across the aortic valve. In these situations, the device can inhibit the leaflets from fully closing, if the force of the device against a leaflet is greater than the contractile force of the leaflet.

SUMMARY

In an Example 1, a percutaneous circulatory support system includes an impeller and a motor operably coupled to the impeller. A controller is operably coupled to the motor, and the controller is configured to: drive the motor, the motor thereby rotating the impeller to cause blood to flow; determine that an operating parameter of the system deviates from a symmetric waveform; and in response to determining that the operating parameter deviates from the symmetric waveform, provide an alert of aortic valve insufficiency.

In an Example 2, the percutaneous circulatory support system of Example 1, wherein the controller is configured to determine that the operating parameter deviates from a square waveform.

In an Example 3, the percutaneous circulatory support system of any of Examples 1-2, wherein the controller is configured to determine that the operating parameter deviates from the symmetric waveform within a cardiac cycle of the patient.

In an Example 4, the percutaneous circulatory support system of any of Examples 1-2, wherein the controller is configured to determine that the operating parameter deviates from the symmetric waveform during the cardiac cycle of the patient by comparing an increase in the operating parameter during systolic contraction to a decrease in the operating parameter following the dicrotic notch.

In an Example 5, the percutaneous circulatory support system of Example 4, wherein comparing the increase in the operating parameter to the decrease in the operating parameter includes high pass filtering the operating parameter to provide a parameter rate; low pass filtering a first portion of the parameter rate to provide an upper envelope corresponding to the increase in the operating parameter; converting a second portion of the parameter rate to a positive parameter rate; low pass filtering the positive parameter rate to provide a lower envelope corresponding to the decrease in the operating parameter; determining a ratio of the upper envelope to the lower envelope; and comparing the ratio to a threshold.

In an Example 6, the percutaneous circulatory support system of Example 5, wherein the threshold is 0.5.

In an Example 7, the percutaneous circulatory support system of any of Examples 5-6, wherein the controller is further configured to apply a saturation operation to the parameter rate.

In an Example 8, the percutaneous circulatory support system of any of Examples 1-7, wherein the controller is further configured to receive feedback from the motor and adjust the operating parameter based on the feedback.

In an Example 9, the percutaneous circulatory support system of any of Examples 1-8, wherein the operating parameter is a commanded voltage provided by the controller to drive the motor.

In an Example 10, the percutaneous circulatory support system of any of Examples 1-9, wherein the operating parameter is an electric current provided to the motor.

In an Example 11, a percutaneous circulatory support system includes an impeller and a motor operably coupled to the impeller. A controller is operably coupled to the motor, and the controller is configured to: provide a commanded voltage to the motor, the motor thereby rotating the impeller to cause blood to flow; high pass filter the commanded voltage to provide a commanded voltage rate; low pass filter a first portion of the commanded voltage rate to provide an upper voltage envelope corresponding to an increase in the commanded voltage; convert a second portion of the commanded voltage rate to a positive voltage rate; low pass filter the positive voltage rate to provide a lower voltage envelope corresponding to a decrease in the commanded voltage; determine a ratio of the upper voltage envelope to the lower voltage envelope; and compare the ratio to a threshold; in response to determining that the ratio is less than the threshold, provide an alert of aortic valve insufficiency.

In an Example 12, the percutaneous circulatory support system of Example 11, wherein the controller is further configured to receive feedback from the motor and adjust the commanded voltage based on the feedback.

In an Example 13, the percutaneous circulatory support system of Example 12, wherein the controller is configured to high pass filter the commanded voltage to provide the commanded voltage rate after adjusting the commanded voltage based on the feedback.

In an Example 14, the percutaneous circulatory support system of any of Examples 11-13, wherein the threshold is 0.5.

In an Example 15, the percutaneous circulatory support system of any of Examples 11-14, wherein the controller is further configured to apply a saturation operation to the commanded voltage rate.

In an Example 16, a percutaneous circulatory support system includes a housing configured to be positioned within a patient. An impeller is carried within the housing, and a motor is operably coupled to the impeller. A controller is operably coupled to the motor, and the controller is configured to: drive the motor, the motor thereby rotating the impeller relative to the housing to cause blood to flow through the housing; determine that an operating parameter of the system deviates from a symmetric waveform; and in response to determining that the operating parameter deviates from the symmetric waveform, provide an alert of aortic valve insufficiency.

In an Example 17, the percutaneous circulatory support system of Example 16, wherein the controller is configured to determine that the operating parameter deviates from a square waveform.

In an Example 18, the percutaneous circulatory support system of Example 16, wherein the controller is configured to determine that the operating parameter deviates from the symmetric waveform within a cardiac cycle of the patient.

In an Example 19, the percutaneous circulatory support system of Example 18, wherein the controller is configured to determine that the operating parameter deviates from the symmetric waveform during the cardiac cycle of the patient by comparing an increase in the operating parameter during systolic contraction to a decrease in the operating parameter following the dicrotic notch.

In an Example 20, the percutaneous circulatory support system of Example 19, wherein comparing the increase in the operating parameter to the decrease in the operating parameter includes: high pass filtering the operating parameter to provide a parameter rate; low pass filtering a first portion of the parameter rate to provide an upper envelope corresponding to the increase in the operating parameter; converting a second portion of the parameter rate to a positive parameter rate; low pass filtering the positive parameter rate to provide a lower envelope corresponding to the decrease in the operating parameter; determining a ratio of the upper envelope to the lower envelope; and comparing the ratio to a threshold.

In an Example 21, the percutaneous circulatory support system of Example 20, wherein the threshold is 0.5.

In an Example 22, the percutaneous circulatory support system of Example 16, wherein the controller is further configured to receive feedback from the motor and adjust the operating parameter based on the feedback.

In an Example 23, the percutaneous circulatory support system of Example 16, wherein the operating parameter is a commanded voltage provided by the controller to drive the motor.

In an Example 24, a percutaneous circulatory support system includes a housing configured to be positioned within a patient, an impeller carried within the housing, and a motor operably coupled to the impeller. A controller is operably coupled to the motor, and the controller is configured to provide a commanded voltage to the motor, the motor thereby rotating the impeller relative to the housing to cause blood to flow through the housing; high pass filter the commanded voltage to provide a commanded voltage rate; low pass filter a first portion of the commanded voltage rate to provide an upper voltage envelope corresponding to an increase in the commanded voltage; convert a second portion of the commanded voltage rate to a positive voltage rate; low pass filter the positive voltage rate to provide a lower voltage envelope corresponding to a decrease in the commanded voltage; determine a ratio of the upper voltage envelope to the lower voltage envelope; and compare the ratio to a threshold; in response to determining that the ratio is less than the threshold, provide an alert of aortic valve insufficiency.

In an Example 25, the percutaneous circulatory support system of Example 24, wherein the controller is further configured to receive feedback from the motor and adjust the commanded voltage based on the feedback.

In an Example 26, the percutaneous circulatory support system of Example 25, wherein the controller is configured to high pass filter the commanded voltage to provide the commanded voltage rate after adjusting the commanded voltage based on the feedback.

In an Example 27, the percutaneous circulatory support system of Example 24, wherein the threshold is 0.5.

In an Example 28, a percutaneous circulatory support system includes a housing, an impeller disposed in the housing, a motor operably coupled to the impeller, and a controller operably coupled to the motor. A method of using the system includes: driving, via the controller, the motor, the motor thereby rotating the impeller to cause blood to flow through the housing; determining, via the controller, that an operating parameter of the system deviates from a symmetric waveform; and providing, via the controller, an alert of aortic valve insufficiency in response to determining that the operating parameter deviates from the symmetric waveform.

In an Example 29, the method of Example 28, wherein determining that the operating parameter deviates from the symmetric waveform includes determining that the operating parameter deviates from a square waveform.

In an Example 30, the method of Example 28, wherein determining that the operating parameter deviates from the symmetric waveform includes determining that the operating parameter deviates from the symmetric waveform within a cardiac cycle of the patient.

In an Example 31, the method of Example 30, wherein determining that the operating parameter deviates from the symmetric waveform includes comparing an increase in the operating parameter during systolic contraction to a decrease in the operating parameter following the dicrotic notch.

In an Example 32, the method of Example 31, wherein comparing, via the controller, the increase in the operating parameter to the decrease in the operating parameter includes: high pass filtering the operating parameter to provide a parameter rate; low pass filtering a first portion of the parameter rate to provide an upper envelope corresponding to the increase in the operating parameter; converting a second portion of the parameter rate to a positive rate; low pass filtering the positive rate to provide a lower envelope corresponding to the decrease in the operating parameter; determining a ratio of the upper envelope to the lower envelope; and comparing the ratio to a threshold.

In an Example 33, the method of Example 28, further including receiving, by the controller, feedback from the motor and adjusting, via the controller, the operating parameter based on the feedback.

In an Example 34, the method of Example 33, wherein adjusting the operating parameter based on the feedback precedes determining that the operating parameter deviates from the symmetric waveform.

In an Example 35, the method of Example 28, wherein the operating parameter is a commanded voltage, and the method further includes providing, via the controller, the commanded voltage to the motor to drive the motor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
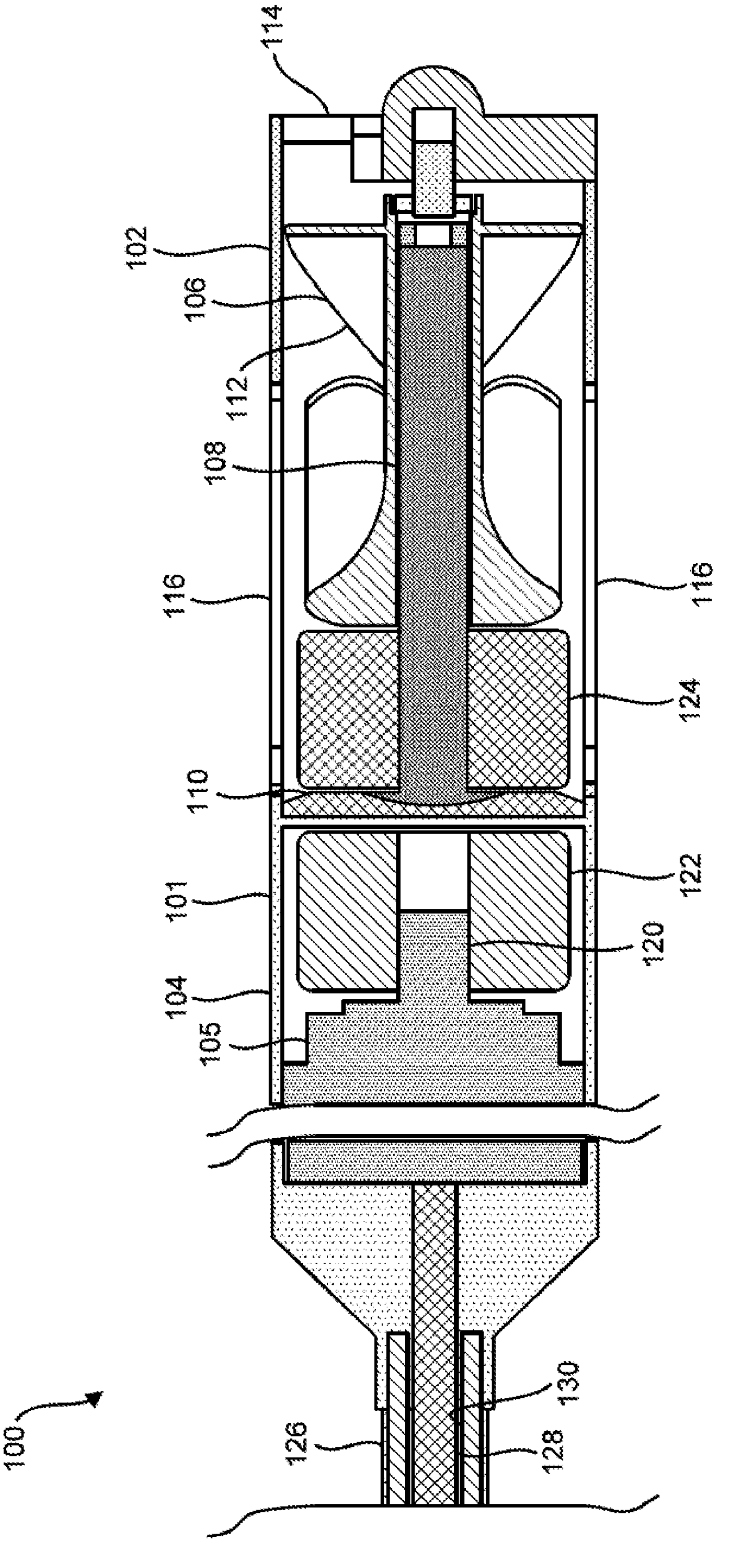
FIG. 1 is a side sectional view of an illustrative percutaneous circulatory support device (also referred to herein, interchangeably, as a "blood pump"), in accordance with embodiments of the subject matter disclosed herein.

While the invention is amenable to various modifications and alternative forms, specific embodiments have been shown by way of example in the drawings and are described in detail herein. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Use of left ventricular support devices can cause aortic valve insufficiency, in which the aortic valve fails to properly seal and isolate the left ventricle and the aorta during diastole. As a result, blood improperly "backflows" from the aorta to the left ventricle, which is also referred to as aortic regurgitation. This can cause increased ventricular afterload, reduced arterial pressure, and/or increased hemolysis, which undermine the effectiveness of such support devices. Moreover, aortic valve insufficiency is often difficult to detect and, as a result, physicians may be unaware of a need to address the condition. Accordingly, certain embodiments of the present disclosure are directed to relatively simple and effective approaches for detecting aortic insufficiency while a left ventricular assist device is in use.

FIG. 1 depicts a partial side sectional view of an illustrative percutaneous circulatory support device 100 (also referred to herein, interchangeably, as a "blood pump") in accordance with embodiments of the subject matter disclosed herein. The device 100 may form part of a percutaneous circulatory support system, together with, for example, a guidewire and an introducer sheath, among other devices. More specifically, the guidewire and the introducer sheath may facilitate percutaneously delivering the device 100 to a target location within a patient, such as within the patient's heart. Alternatively, the device 100 may be delivered to a different target location within a patient.

With continued reference to FIG. 1, the device 100 generally includes a housing 101 that includes an impeller housing 102 and a motor housing 104. In some embodiments, the impeller housing 102 and the motor housing 104 may be integrally or monolithically constructed. In other embodiments, the impeller housing 102 and the motor housing 104 may be separate components configured to be removably or permanently coupled. In some embodiments, the blood pump 100 may lack a separate motor housing 104 and the impeller housing 102 may be coupled directly to a motor 105 described herein, or the motor housing 104 may be integrally constructed with the motor 105 described herein.

The impeller housing 102 carries an impeller assembly 106 therein. The impeller assembly 106 includes an impeller shaft 108 that is rotatably supported by at least one bearing, such as a bearing 110. The impeller assembly 106 also includes an impeller 112 that rotates relative to the impeller housing 102 to drive blood through the device 100. More specifically, the impeller 112 causes blood to flow from a blood inlet 114 formed on the impeller housing 102, through the impeller housing 102, and out of a blood outlet 116 formed on the impeller housing 102. In some embodiments and as illustrated, the impeller shaft 108 and the impeller 112 may be separate components, and in other embodiments the impeller shaft 108 and the impeller 112 may be integrated. In some embodiment and as illustrated, the inlet 114 and/or the outlet 116 may each include multiple apertures. In other embodiments, the inlet 114 and/or the outlet 116 may each include a single aperture. In some embodiments and as illustrated, the inlet 114 may be formed on an end portion of the impeller housing 102 and the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula, and the cannula may receive and deliver blood to the inlet 114.

With continued reference to FIG. 1, the motor housing 104 carries the motor 105, and the motor 105 is operably coupled to and configured to rotatably drive the impeller 112. In the illustrated embodiment, the motor 105 rotates a drive shaft 120, which is coupled to a driving magnet 122. Rotation of the driving magnet 122 causes rotation of a driven magnet 124, which is connected to and rotates together with the impeller assembly 106. More specifically, in embodiments incorporating the impeller shaft 108, the impeller shaft 108 and the impeller 112 are configured to rotate with the driven magnet 124. In other embodiments, the motor 105 may couple to the impeller assembly 106 via other components.

The motor housing 104 couples to a catheter 126 opposite the impeller housing 102. The catheter 126 may couple to the motor housing 104 in various manners, such as laser welding, soldering, or the like. The catheter 126 extends proximally away from the motor housing 104. The catheter 126 carries a motor cable 128 within a main lumen 130, and the motor cable 128 may operably couple the motor 105 to a controller (shown elsewhere) and/or a power source.

Figure 2:
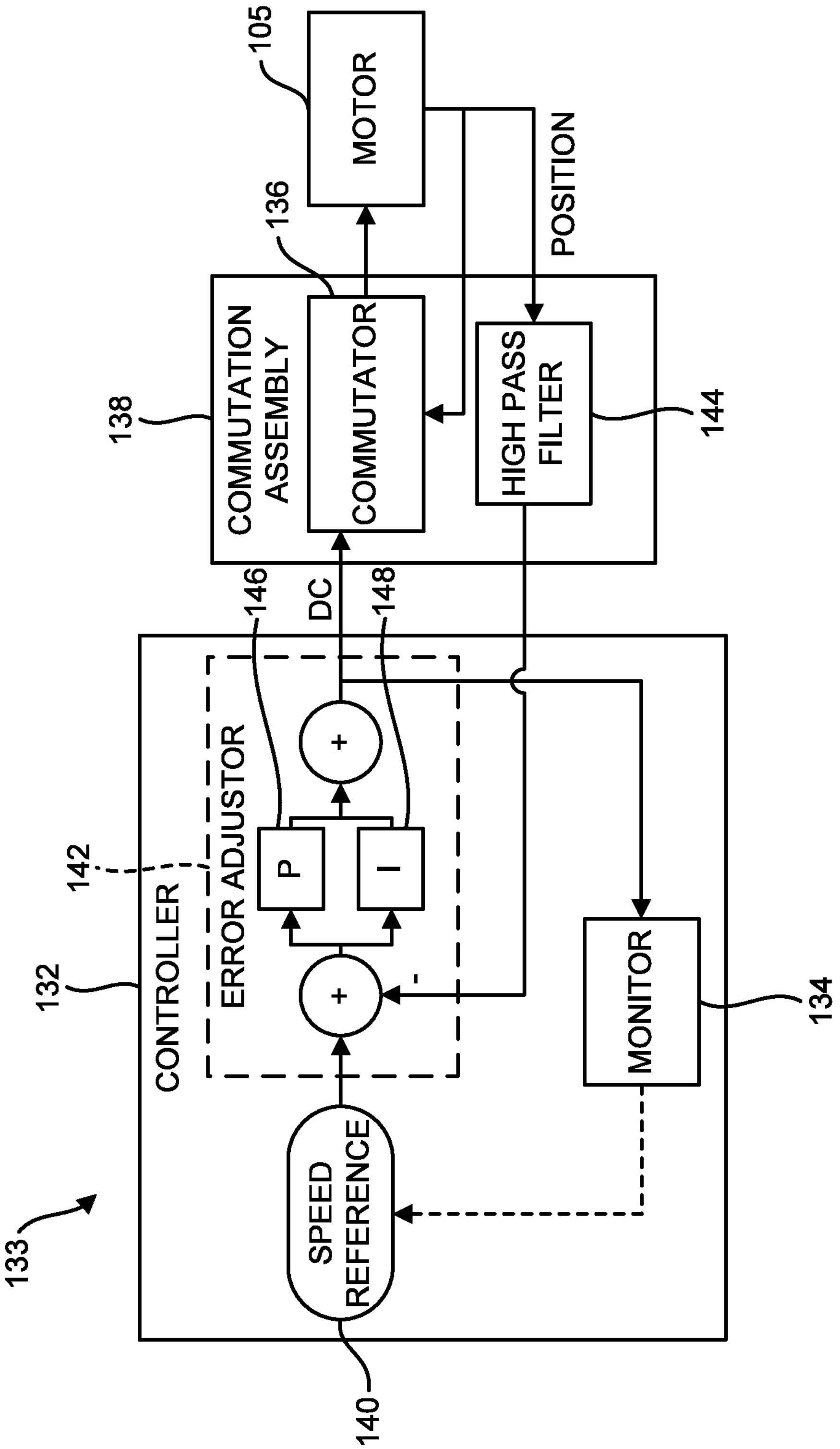
FIG. 2 is a schematic view of electronic components of the percutaneous circulatory support device of FIG. 1, in accordance with embodiments of the subject matter disclosed herein.

With further reference to FIG. 1 and additional reference to FIG. 2, the controller 132 may be operably coupled to the motor 105 and configured to control the motor 105. In some embodiments, the controller 132 may be disposed within the motor housing 104. In other embodiments, the controller 132 may be disposed outside of the motor housing 104 (for example, in an independent housing of the system 133, etc.) and coupled to the motor 105 via the motor cable 128. In some embodiments, the controller 132 may include multiple components, one or more of which may be disposed within the motor housing 104. According to embodiments, the controller 132 may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. As such, the controller 132 can be an integrated circuit (such as an ASIC or other type of circuitry) programmed to carry out one or more functions described herein. Although the controller 132 is referred to herein in the singular, the controller may be implemented in multiple instances, distributed across multiple computing devices, instantiated within multiple virtual machines, and/or the like.

With continued reference to FIG. 2, the system 133 also includes a commutation assembly 138 that operably couples the controller 132 and the motor 105. As illustrated, the commutation assembly 138 may be separate from the controller 132 and the motor 105 (for example, in an independent housing of the system 133, etc.). In other embodiments, the commutation assembly 138 may be disposed within the motor housing 104 and/or combined with the controller 132.

Generally, the controller 132 is configured to analyze one or more operating parameters of the device 100 to detect aortic valve insufficiency in a patient. For example, the controller 132 includes a monitor 134 that analyzes the commanded voltage the controller 132 provides to the motor 105, via a commutator 136 of a commutation assembly 138, to drive the motor 105 at a reference speed 140. The controller 132 also includes an error adjustor 142 that adjusts the commanded voltage based on feedback received from the motor 105, via a high pass filter 144 of the commutation assembly 138. Illustratively, the error adjustor 142 includes proportional error adjustment 146 and integral error adjustment 148. In other embodiments, the controller 132 is configured to analyze one or more additional or alternative operating parameters of the device 100 to detect aortic valve insufficiency in a patient. Such operating parameters include, for example, motor current, motor speed, motor torque, and sensed arterial or ventricular pressure.

Figure 3:
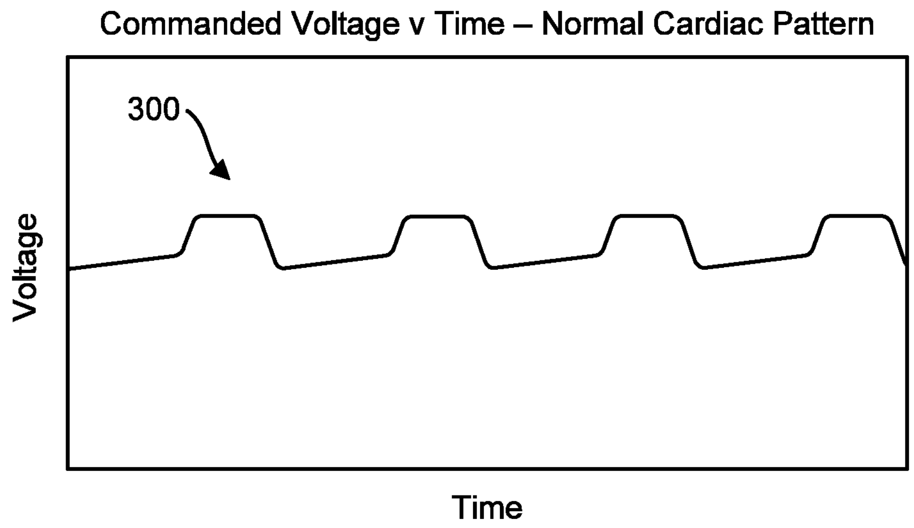
FIG. 3 is a graph of commanded voltage of a percutaneous circulatory support device versus time for a normal cardiac pattern.
Figure 4:
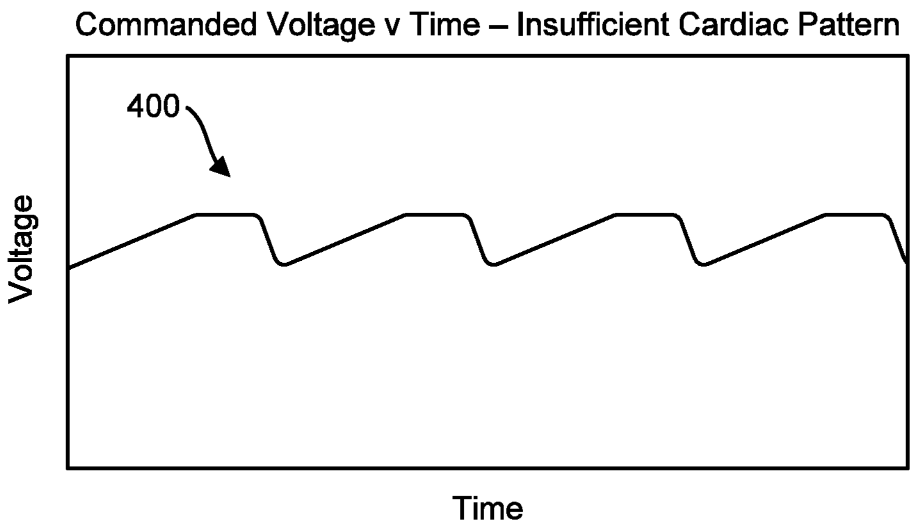
FIG. 4 is a graph of commanded voltage of a percutaneous circulatory support device versus time for an insufficient cardiac pattern.

In some embodiments, the monitor 134 analyzes the shape of the operating parameter's waveform, such as the commanded voltage's waveform, which varies based on the pressure gradient across the aortic valve, to detect aortic valve insufficiency. More specifically, for a normal cardiac pattern (that is, in which aortic valve insufficiency is not present) and for a fixed velocity control, the commanded voltage rapidly increases during systolic contraction (when pressure in the left ventricle rapidly increases), and the commanded voltage rapidly decreases following the dicrotic notch (when pressure in the left ventricle rapidly decreases, between the closing of the aortic valve and the opening of the mitral valve). As illustrated in FIG. 3, these rapid voltage changes provide the commanded voltage with a symmetric waveform 300, more specifically a square waveform, over these portions of the cardiac pattern. Stated another way, the rate at which the voltage increases is substantially similar to the rate at which the voltage decreases. By detecting a symmetric waveform, the monitor 134 may determine that aortic valve insufficiency is not present. In contrast, for an insufficient cardiac pattern (that is, in which aortic valve insufficiency is present and blood improperly backflows from the aorta to the left ventricle), the commanded voltage more gradually increases before and during systolic contraction, but the commanded voltage nevertheless rapidly decreases following the dicrotic notch. As a result and as shown in FIG. 4, the voltage changes provide the commanded voltage with an asymmetric waveform 400, such as a non-square waveform (for example, a sawtooth-like waveform). By detecting such a waveform, the monitor 134 may determine that aortic valve insufficiency is present.

Figure 5:
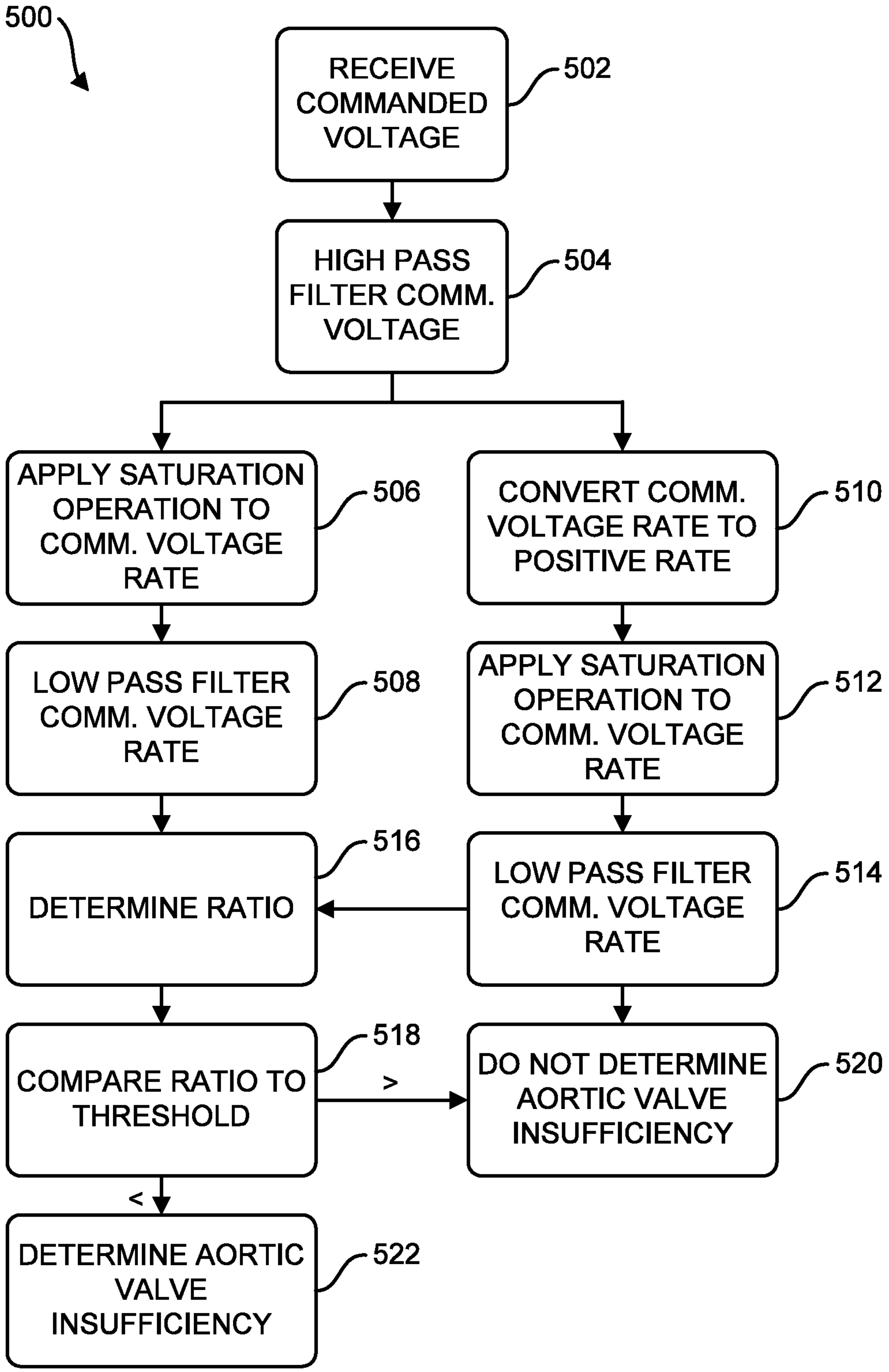
FIG. 5 is a flow diagram of a method of operating a percutaneous circulatory support device and detecting aortic valve insufficiency, in accordance with embodiments of the subject matter disclosed herein.

Referring to FIG. 5, an illustrative method 500 of operating the percutaneous circulatory support system 133 and detecting aortic valve insufficiency is as follows. First, the controller 132 provides a commanded voltage to the motor 105, and the motor 105 thereby rotates the impeller 112 to cause blood to flow through the housing 101. As shown at block 502, the monitor 134 also receives the commanded voltage. At block 504, the commanded voltage is high pass filtered, via a high pass filter of the controller 132, to provide a commanded voltage rate. Then, at block 506, a saturation operation is applied to the commanded voltage rate. At block 508, a first portion of the commanded voltage rate, corresponding to the voltage increase described herein, is low pass filtered, via a low pass filter of the controller 132, to provide a first or upper voltage envelope. In parallel to blocks 506 and 508, at block 510, a second portion of the commanded voltage rate, corresponding to the voltage decrease described herein, is converted to a positive voltage rate (for example, by multiplying by negative one). At block 512, a saturation operation is applied to the positive voltage rate. At block 514, the positive voltage rate is low pass filtered, via a low pass filter of the controller 132, to provide a second or lower voltage envelope. At block 516, a ratio of the upper voltage envelope to the lower voltage envelope is determined. Next, at block 518, the ratio is compared to a threshold (for example, of 0.5). If the ratio is greater than the threshold, at block 520, it is determined that aortic valve insufficiency is not present. If the ratio is less than the threshold, at block 522, it is determined that aortic valve insufficiency is present. In some embodiments, the system 133 repeats the method frequently, more specifically, during each cycle of the cardiac pattern of the patient, or the system 133 repeats the method continuously, or conducts analog or emulates analog computations.

If aortic valve insufficiency is detected (for example, over multiple cycles of the cardiac pattern within a specific time period, or in a single cycle of the cardiac pattern), the system 133 provides an alert (for example, a visual and/or audio alert) to medical practitioner, and the medical practitioner may then modify operation of the system 133. More specifically, the medical practitioner may make an informed decision on how to best proceed which may include continued use of device, modify operational settings of the system 133 (for example, the speed of the motor 105), reposition the device 100 within the patient, or discontinue use of the system 133.

Figure 6:
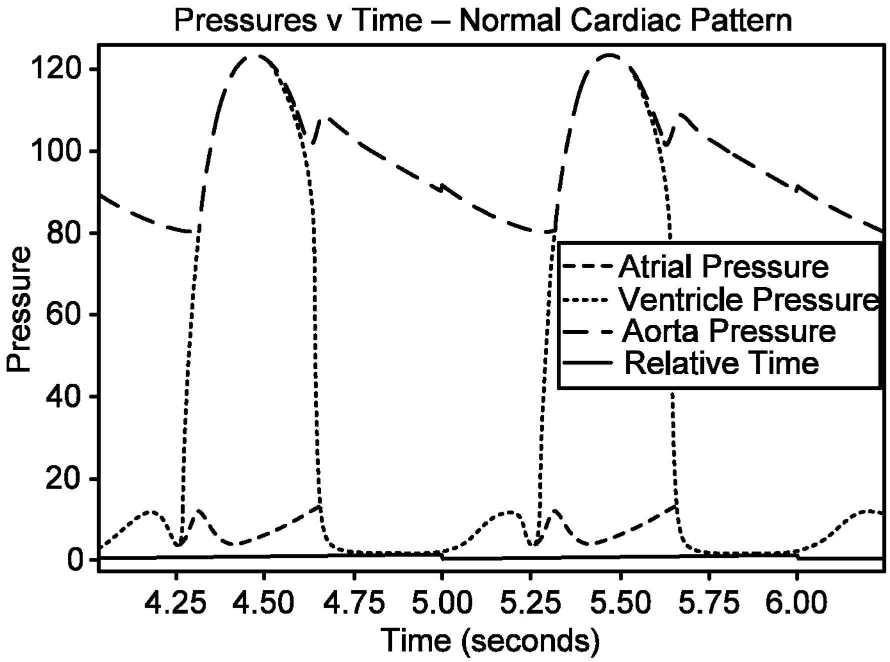
FIG. 6 is a graph of simulated pressures within a patient versus time for a normal cardiac pattern.
Figure 7:
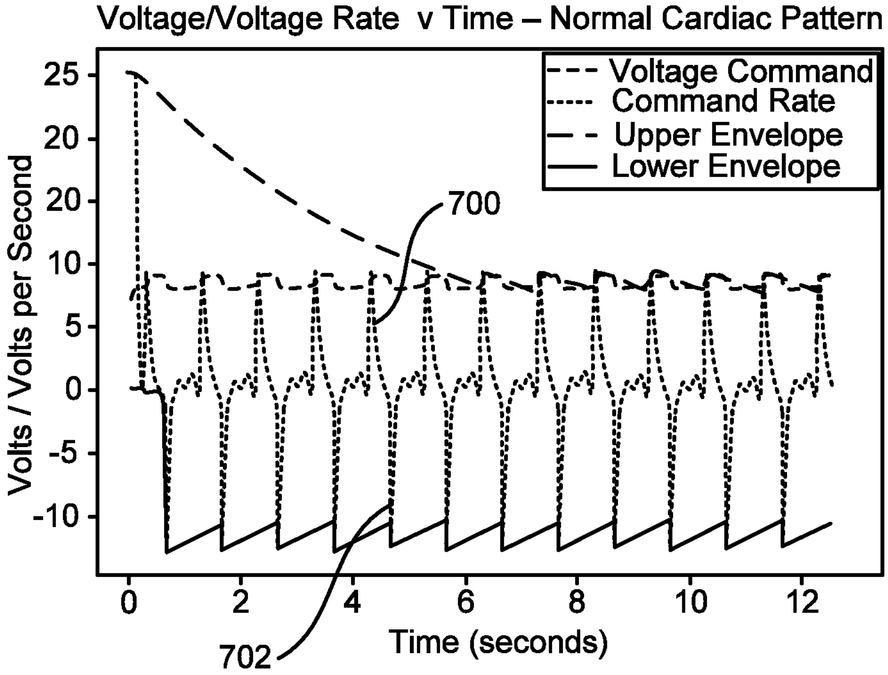
FIG. 7 is a graph of simulated voltages and voltage rates versus time corresponding to the simulated pressures of FIG. 6.
Figure 8:
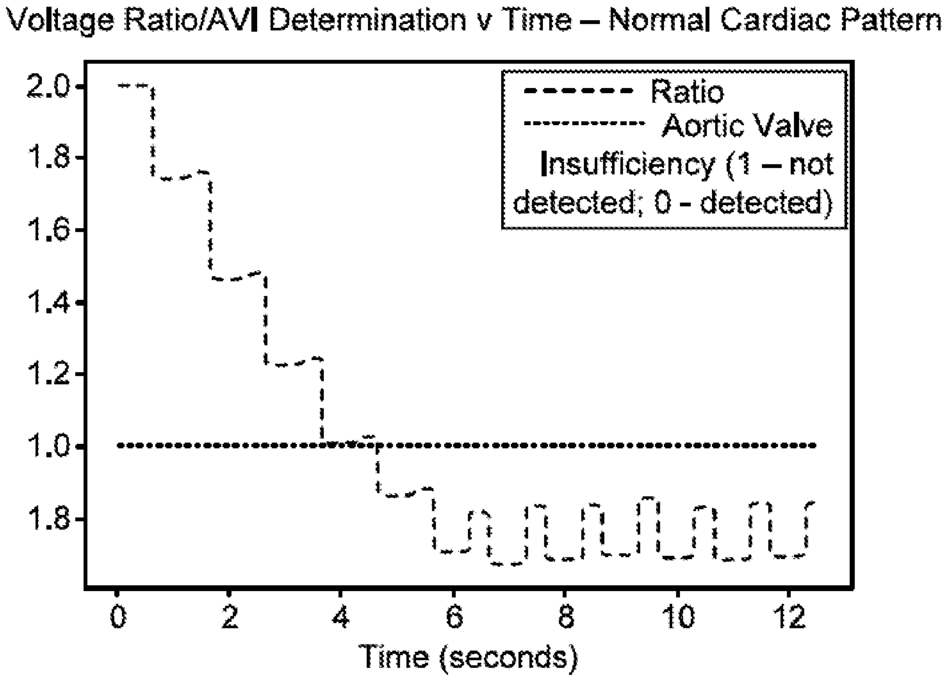
FIG. 8 is a graph of simulated voltage ratios and aortic valve insufficiency determinations corresponding to the simulated voltages and voltage rates of FIG. 7.

FIG. 6 illustrates simulated pressures within a patient during a normal cardiac pattern, more specifically about two cycles in such a pattern. As illustrated, there is a relatively large pressure gradient between the aorta and the left ventricle before systolic contraction (for example, before 4.25 seconds and 5.25 seconds) because the aortic valve properly closes and isolates the aorta and the left ventricle. FIG. 7 illustrates simulated voltages and voltage rates during a normal cardiac pattern, more specifically about twelve cycles in such a pattern. The lower voltage envelope is illustrated as a negative value for clarity, instead of a positive value as described herein. FIG. 7 includes, among other time periods, the time period illustrated in FIG. 6. During systolic contraction (for example, before 4.25 seconds and 5.25 seconds), the commanded voltage rate includes a relatively large positive spike 700. Following the dicrotic notch, (for example, at about 4.5 seconds and 5.5 seconds), the commanded voltage rate includes a relatively large negative spike 702. After an initial start-up period (for example, after about 6 seconds), the upper envelope voltage and the lower envelope voltage are consistently determined based on the positive spikes 700 and the negative spikes 702, respectively. FIG. 8 illustrates simulated voltage ratios, of the upper envelope voltage to the lower envelope voltage, and aortic valve insufficiency determinations during a normal cardiac pattern, more specifically about twelve cycles in such a pattern. FIG. 8 includes the same time period illustrated in FIG. 7. After the initial start-up period (for example, after about 6 seconds), the ratio is consistently determined to be greater than the threshold (for example, 0.5), and aortic valve insufficiency is not detected.

Figure 9:
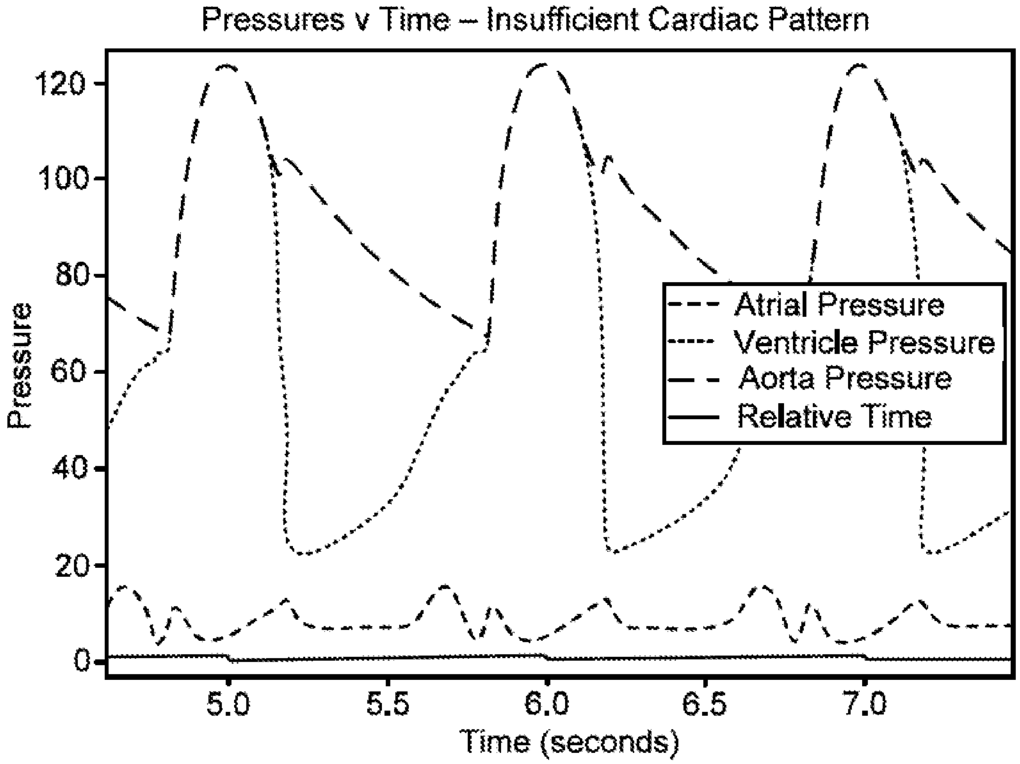
FIG. 9 is a graph of simulated pressures within a patient versus time for an insufficient cardiac pattern.
Figure 10:
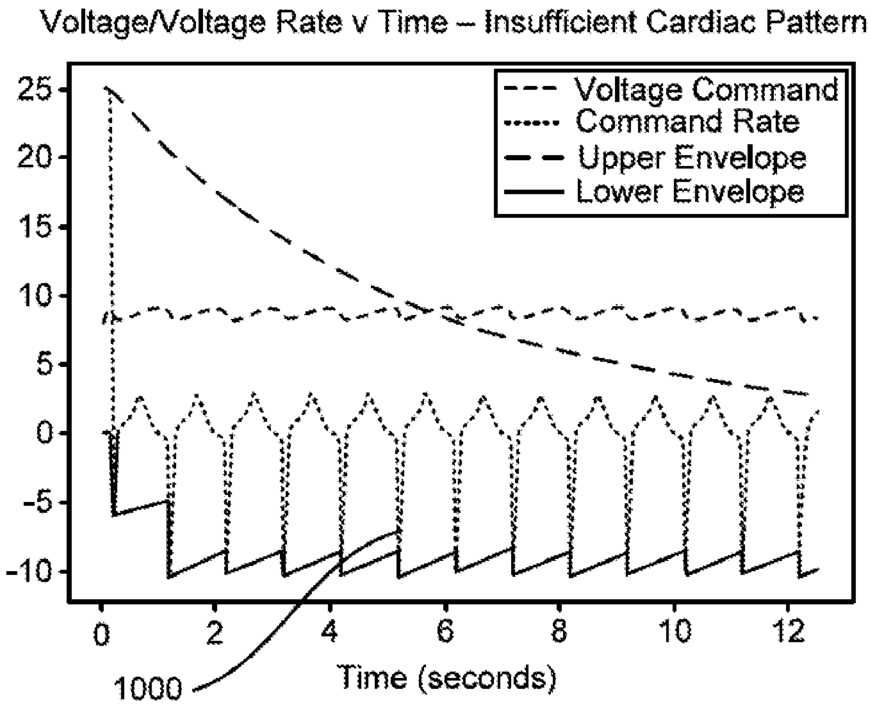
FIG. 10 is a graph of simulated voltages and voltage rates versus time corresponding to the simulated pressures of FIG. 9.
Figure 11:
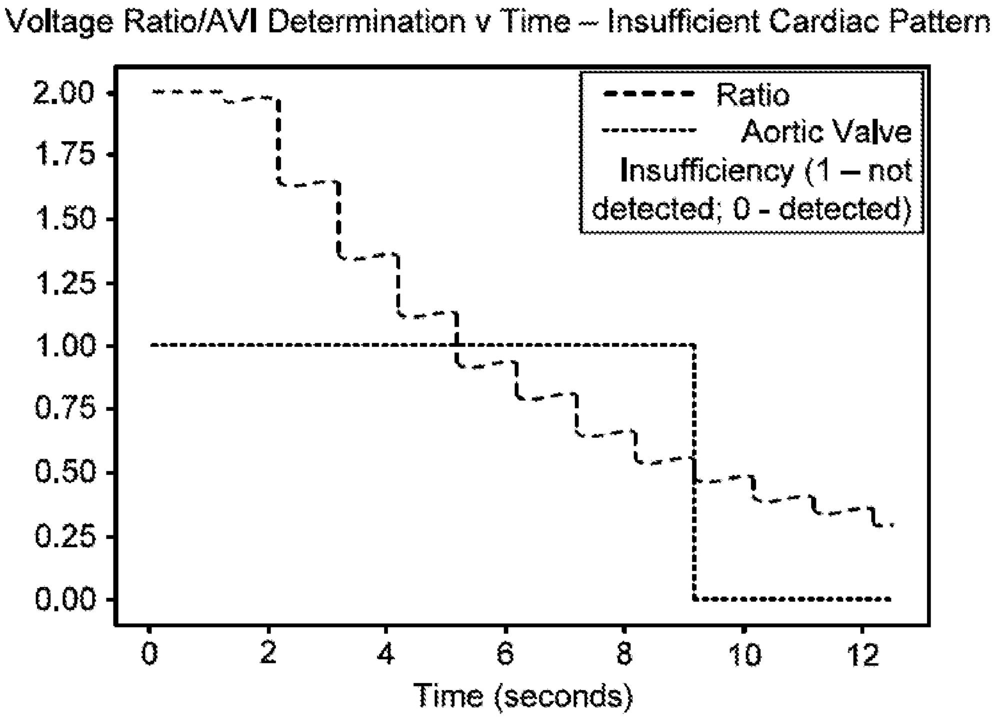
FIG. 11 is a graph of simulated voltage ratios and aortic valve insufficiency determinations corresponding to the simulated voltages and voltage rates of FIG. 10.

FIG. 9 illustrates simulated pressures within a patient during an insufficient cardiac pattern, more specifically about three cycles in such a pattern. As illustrated, the pressure in the aorta and the left ventricle nearly equalizes before systolic contraction (for example, before 4.75 seconds, 5.75 seconds, and 6.75 seconds) because the aortic valve does not properly close and thereby permits blood to backflow from the aorta to the left ventricle. FIG. 10 illustrates simulated voltages and voltage rates during an insufficient cardiac pattern, more specifically about twelve cycles in such a pattern. The lower voltage envelope is illustrated as a negative value for clarity, instead of a positive value as described herein. FIG. 10 includes, among other time periods, the time period illustrated in FIG. 9. During systolic contraction (for example, at about 4.75 seconds, 5.75 seconds, and 6.75 seconds), the commanded voltage rate includes a relatively large positive spike as shown in FIG. 7. Following the dicrotic notch, (for example, at about 5.2 seconds, 6.2 seconds, and 7.2 seconds), the commanded voltage rate includes a relatively large negative spike 1000. FIG. 11 illustrates simulated voltage ratios, of the upper envelope voltage to the lower envelope voltage, and aortic valve insufficiency determinations during an insufficient cardiac pattern, more specifically about twelve cycles in such a pattern. FIG. 11 includes the same time period illustrated in FIG. 10. At about 9 seconds, the ratio falls below the threshold (for example, 0.5) and, as a result, aortic valve insufficiency is detected.

As described briefly herein, in some embodiments the controller 132 is configured to analyze one or more additional or alternative operating parameters of the device 100 to detect aortic valve insufficiency in a patient. In embodiments in which speed is tightly controlled, the motor current and torque will both have waveforms similar to the voltage, and the methods described herein can be applied to current and/or torque and thereby used to detect aortic insufficiency. As yet another example, in some embodiments, a distal portion of the device 100 includes a pressure sensor configured to be disposed in the arterial blood stream and/or left ventricle. A pressure waveform determined via the sensor would be similar to the voltage, torque, current, and motor speed waveforms described herein, and the method described herein could be applied to the pressure waveform to detect aortic insufficiency. As another example, in some embodiments, speed of the motor 105 may be loosely controlled. In these embodiments, the commanded voltage will remain relatively constant and the motor speed will vary significantly. In such embodiments, the method described herein can be applied to the motor speed feedback to detect aortic insufficiency.

In other embodiments, the system 133 may determine that the commanded voltage, torque, current, or motor speed deviates from a symmetric waveform, and thereby detect aortic valve insufficiency, in other manners. For example, in some embodiments a neural network may be trained to recognize an asymmetrical waveform and thereby detect aortic valve insufficiency. As another example, in some embodiments convolution may be used to determine the presence of an asymmetrical waveform and thereby detect aortic valve insufficiency. As another example, in some embodiments linear programming may be used to directly calculate the slopes of the waveform, and thereby determine the presence an asymmetrical waveform and detect aortic valve insufficiency.

In some embodiments, the controller 132 is configured to analyze one or more operating parameters of the device 100 in other manners to detect aortic valve insufficiency in a patient. For example, the controller 132 may monitor one or more operating parameters of the device 100 (such as the commanded voltage, torque, current, motor speed, and/or sensed arterial or ventricular pressure). If the one or more operating parameters deviate from an expected range during one or more specific portions of the cardiac cycle (for example, diastole), the controller 132 detects aortic valve insufficiency. As a more specific example, the controller 132 may detect aortic valve insufficiency if left ventricular pressure is greater than 30 mmHg and/or aortic pressure is less than 60 mmHg at the end of diastole. As another example, the controller 132 may determine the first derivative(s) of one or more operating parameters of the device 100 (such as the commanded voltage, torque, current, motor speed, and/or sensed arterial or ventricular pressure) with respect to time and detect aortic valve insufficiency if one or more of the first derivatives exceeds a maximum threshold or falls below a minimum threshold. As yet another example, the controller 132 may determine the maximum rate(s) of increase of one or more operating parameters of the device 100 (such as the commanded voltage, torque, current, motor speed, and/or sensed arterial or ventricular pressure). The controller 132 may detect aortic valve insufficiency if one or more of the maximum rate(s) of increase falls below a minimum threshold.

Various modifications and additions can be made to the exemplary embodiments discussed without departing from the scope of the present invention. For example, while the embodiments described herein refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A percutaneous circulatory support system, comprising:

a housing configured to be positioned within a patient;

an impeller carried within the housing;

a motor operably coupled to the impeller; and a controller operably coupled to the motor, the controller being configured to:

drive the motor, the motor thereby rotating the impeller relative to the housing to cause blood to flow through the housing;

detect an aortic valve insufficiency in the patient based on a determination that an operating parameter of the motor deviates from a symmetric waveform, the symmetric waveform having a rate of increase in the operating parameter of the motor that is symmetric with a rate of decrease of the operating parameter of the motor; and in response to determining that the operating parameter deviates from the symmetric waveform, provide an alert of aortic valve insufficiency.

2. The percutaneous circulatory support system of claim 1, wherein the controller is configured to determine that the operating parameter deviates from a square waveform.

3. The percutaneous circulatory support system of claim 1, wherein the controller is configured to determine that the operating parameter deviates from the symmetric waveform within a cardiac cycle of the patient.

4. The percutaneous circulatory support system of claim 3, wherein the controller is configured to determine that the operating parameter deviates from the symmetric waveform during the cardiac cycle of the patient by comparing an increase in the operating parameter during systolic contraction to a decrease in the operating parameter following the dicrotic notch.

5. The percutaneous circulatory support system of claim 4, wherein comparing the increase in the operating parameter to the decrease in the operating parameter comprises:

high pass filtering the operating parameter to provide a parameter rate;

low pass filtering a first portion of the parameter rate to provide an upper envelope corresponding to the increase in the operating parameter;

converting a second portion of the parameter rate to a positive parameter rate;

low pass filtering the positive parameter rate to provide a lower envelope corresponding to the decrease in the operating parameter;

determining a ratio of the upper envelope to the lower envelope; and comparing the ratio to a threshold.

6. The percutaneous circulatory support system of claim 5, wherein the threshold is 0.5.

7. The percutaneous circulatory support system of claim 1, wherein the controller is further configured to receive feedback from the motor and adjust the operating parameter based on the feedback.

8. The percutaneous circulatory support system of claim 1, wherein the operating parameter is a commanded voltage provided by the controller to drive the motor.

9. A percutaneous circulatory support system, comprising:

a housing configured to be positioned within a patient;

an impeller carried within the housing;

a motor operably coupled to the impeller; and a controller operably coupled to the motor, the controller being configured to:

provide a commanded voltage to the motor, the motor thereby rotating the impeller relative to the housing to cause blood to flow through the housing;

high pass filter the commanded voltage to provide a commanded voltage rate;

low pass filter a first portion of the commanded voltage rate to provide an upper voltage envelope corresponding to an increase in the commanded voltage;

convert a second portion of the commanded voltage rate to a positive voltage rate;

low pass filter the positive voltage rate to provide a lower voltage envelope corresponding to a decrease in the commanded voltage;

determine a ratio of the upper voltage envelope to the lower voltage envelope; and compare the ratio to a threshold;

in response to determining that the ratio is less than the threshold, provide an alert of aortic valve insufficiency.

10. The percutaneous circulatory support system of claim 9, wherein the controller is further configured to receive feedback from the motor and adjust the commanded voltage based on the feedback.

11. The percutaneous circulatory support system of claim 10, wherein the controller is configured to high pass filter the commanded voltage to provide the commanded voltage rate after adjusting the commanded voltage based on the feedback.

12. The percutaneous circulatory support system of claim 9, wherein the threshold is 0.5.

13. A method of operating a percutaneous circulatory support system, the system comprising a housing, an impeller disposed in the housing, a motor operably coupled to the impeller, and a controller operably coupled to the motor, the method comprising:

driving, via the controller, the motor, the motor thereby rotating the impeller to cause blood to flow through the housing;

detecting an aortic valve insufficiency in a patient based on determining, via the controller, that an operating parameter of the motor deviates from a symmetric waveform, the symmetric waveform having a rate of increase in the operating parameter of the motor that is symmetric with a rate of decrease of the operating parameter of the motor; and providing, via the controller, an alert of aortic valve insufficiency in response to determining that the operating parameter deviates from the symmetric waveform.

14. The method of claim 13, wherein determining that the operating parameter deviates from the symmetric waveform comprises determining that the operating parameter deviates from a square waveform.

15. The method of claim 13, wherein determining that the operating parameter deviates from the symmetric waveform comprises determining that the operating parameter deviates from the symmetric waveform within a cardiac cycle of the patient.

16. The method of claim 15, wherein determining that the operating parameter deviates from the symmetric waveform comprises comparing an increase in the operating parameter during systolic contraction to a decrease in the operating parameter following the dicrotic notch.

17. The method of claim 16, wherein comparing, via the controller, the increase in the operating parameter to the decrease in the operating parameter comprises:

high pass filtering the operating parameter to provide a parameter rate;

low pass filtering a first portion of the parameter rate to provide an upper envelope corresponding to the increase in the operating parameter;

converting a second portion of the parameter rate to a positive rate;

low pass filtering the positive rate to provide a lower envelope corresponding to the decrease in the operating parameter;

determining a ratio of the upper envelope to the lower envelope; and comparing the ratio to a threshold.

18. The method of claim 13, further comprising receiving, by the controller, feedback from the motor and adjusting, via the controller, the operating parameter based on the feedback.

19. The method of claim 18, wherein adjusting the operating parameter based on the feedback precedes determining that the operating parameter deviates from the symmetric waveform.

20. The method of claim 13, wherein the operating parameter is a commanded voltage, and the method further comprises providing, via the controller, the commanded voltage to the motor to drive the motor.

* * * * *